United States Patent
Li et al.

(10) Patent No.: US 6,698,134 B1
(45) Date of Patent: Mar. 2, 2004

(54) METHOD OF CULTIVATING FRESH SPIRULINA AT HOME AND DEVICE THEREOF

(75) Inventors: Hengguang Li, Beijing (CN); Hongjun Hu, Hubei (CN); Yinglong Chen, Beijing (CN)

(73) Assignee: Succeed Hi-Tech Industrialization Scale-up Assemblies Co., Ltd., Beijing (CN)

( * ) Notice: Subject to any disclaimer, the term of this patent is extended or adjusted under 35 U.S.C. 154(b) by 0 days.

(21) Appl. No.: 09/831,823

(22) PCT Filed: Nov. 16, 1999

(86) PCT No.: PCT/CN99/00191

§ 371 (c)(1), (2), (4) Date: Aug. 15, 2001

(87) PCT Pub. No.: WO00/29546

PCT Pub. Date: May 25, 2000

(30) Foreign Application Priority Data

Nov. 16, 1998 (CN) .................................. 98124744 A

(51) Int. Cl.⁷ .......................... A01G 7/00; A01H 13/00
(52) U.S. Cl. ..................... 47/1.4; 435/257.1; 435/283.1; 119/245
(58) Field of Search .................... 47/1.4; 435/257.1, 435/283.1

(56) References Cited

U.S. PATENT DOCUMENTS

| | | | | |
|---|---|---|---|---|
| 2,815,607 A | * | 12/1957 | Schroeder | |
| 3,403,471 A | * | 10/1968 | Clement et al. | |
| 4,473,970 A | * | 10/1984 | Hills | 47/1.4 |
| 5,121,708 A | * | 6/1992 | Nuttle | 119/3 |
| 5,958,761 A | * | 9/1999 | Yogev et al. | 435/292.1 |
| 6,156,561 A | * | 12/2000 | Kodo et al. | 435/257.1 |
| 6,370,815 B1 | * | 4/2002 | Skill et al. | 47/14 |

FOREIGN PATENT DOCUMENTS

| | | | | |
|---|---|---|---|---|
| CN | 1098246 | * | 2/1995 | A01G/33/00 |
| CN | 97240920 | * | 6/1997 | C12M/1/00 |
| CN | 97240920.3 | | 12/1998 | |
| JP | 403083563 A | * | 4/1989 | A23L/1/48 |
| JP | 403254674 A | * | 11/1991 | C12N/1/12 |
| JP | 07289201 A | * | 4/1994 | A23F/3/16 |

OTHER PUBLICATIONS http:/welcom–to.chiangmai–chiangrai.com/boonsom_farm.htm, Welcome to Chiangmai & Chiangrai, Boonsom's Spirulina Farm 2 pages.*
http://www.spirulinasource.com/microfarms, The New Community and Family Microfarms, 6 pages.*

* cited by examiner

Primary Examiner—Peter M. Poon
Assistant Examiner—Andrea M. Valenti
(74) Attorney, Agent, or Firm—Finnegan, Henderson, Farabow, Garrett & Dunner, L.L.P.

(57) ABSTRACT

The present invention discloses a method and an apparatus for cultivating and consuming fresh Spirulina at home. The method comprises species selection of Spirulina for cultivation at home, cultivation environment and apparatus conditions, cultivation and maintenance of Spirulina, collection of fresh Spirulina, consumption and storage of fresh Spirulina. The invention changes the situations that Spirulina are only produced in plants and the finished products of Spirulina are bought in stores or hospitals. The invention not only enables the nutrients of Spirulina to be stored and utilized much completely, but also comprehensively utilizes this original biological resource and characteristics of Spirulina (such as absorption of carbon dioxide, release of fresh oxygen and production of high-protein nutrient source) and thus develops and popularizes much quickly the edible Spirulina to meet the needs of the public to health foods.

10 Claims, 1 Drawing Sheet

METHOD OF CULTIVATING FRESH SPIRULINA AT HOME AND DEVICE THEREOF

BACKGROUND OF THE INVENTION

1. Field of the Invention

The present invention relates to a method and an apparatus for cultivating and consuming fresh Spirulina at home, belonging to a method and an apparatus for cultivating and consuming fresh Spirulina on a small scale (it means in a broad sense any small-scale vessel cultivation except laboratory-scale and plant-scale cultivation).

2. Disclosure of the Prior Art

Spirulina has already been generally acknowledged as "the best nourishing health food for human consumption" all over the world. Many international authoritative organizations such as Food and Agriculture Organization of the United Nations (FAO), World Health Organization (WHO), Food and Drug Administration (FDA) etc, have reached a final conclusion on this point. In China, the State Council has placed on "the seventh national five-year plan" the goal to develop Spirulina and supplement nutritive protein for human consumption.

Spirulina is a kind of aquatic organism that has existed for more than three billion years. The present worldwide Spirulina source is very limited. The existing commercially available Spirulina is produced by plant-scale cultivation followed by processing into finished products, such as tablets, capsules, powders and drinks etc., which meet the needs of transportation and storage and are ultimately supplied to consumers. Up till now, the techniques adopted all over the world are plant-scale cultivation followed by commercial processing. The plant-scale cultivation is mainly an open-air scale cultivation utilizing natural conditions, such as sunlight, ambient temperature and timely seasons, after which Spirulina is harvested collectively and subjected to rinse, dehydration, drying, tabletting or filling and then enters the consumption market as commercial end products. However, not only the plant-scale cultivation and commercial processing of Spirulina need huge investments resulting in the high prices of Spirulina products, but also Spirulina loses some of its nutritive ingredients after being dried. Moreover, often due to the defects in the processing techniques, some ingredients deteriorate, resulting in a foreign flavor in the finished products, which is difficult for an ordinary person to accept.

SUMMARY OF THE INVENTION

The object of the present invention is to provide a method and an apparatus for cultivating and consuming fresh Spirulina at home, to comprehensively utilize the biological characteristics of viable Spirulina, such as absorption of carbon dioxide and release of biological oxygen, and thus to remake the environment and improve the general level of human health.

By changing both the method for producing Spirulina and the method for consuming Spirulina, the present invention enables people to cultivate and consume fresh Spirulina at home, changes high-grade nourishing health foods into daily foods that every one and every family can afford. At the same time, the present invention avoids the damage to the public caused by counterfeit health foods.

The object of the present invention is achieved by the method and the apparatus described bellow:

A method for cultivating and consuming fresh Spirulina at home, comprising species selection of Spirulina for cultivation at home, culture conditions for cultivation at home, cultivation and maintenance method, collection and harvest of viable Spirulina cells, consumption of fresh Spirulina, storage of fresh Spirulina etc., characterized in that:

(1) Species of Spirulina: Spirulina platensis and Spirulina maxima for cultivation at home;

(2) Culture conditions: inorganic compound nutrients and clean fresh water are selected as culture medium; an alkaline resisting, non-toxic apparatus equipped with a light source, a heat source and a stirring means;

(3) Cultivation and maintenance of Spirulina: the culture medium is first dissolved in water, the pH of the solution being 8–11, and then the Spirulina seed is inoculated into the solution, water temperature during the normal cultivation period being 25–40° C.; If there are Spirulina cells adhering to the vessel wall, brushing them off the wall with a brush to impel them to move;

(4) Collection of viable Spirulina: part of Spirulina is collected and harvested by filtration using a fine filter screen, the remaining part is further cultivated; if necessary, old Spirulina and precipitate are removed by using a coarse filter screen;

(5) Consumption of fresh Spirulina: the filtered-out fresh Spirulina is first rinsed with water to remove the remaining culture solution, and then consumed directly after being added to various kinds of drinks or other foods;

(6) Storage of fresh Spirulina: after rinsing with water the fresh Spirulina is directly stored for further use by freezing, or formulated into a paste with cold drinking water and then stored by freezing.

The above-mentioned culture medium comprises the following ingredients (based on 1 liter of culture solution):

| | | | |
|---|---|---|---|
| $K_2HPO_4$, $(Na_2)HPO_4$ or $KH_2PO_4$, $NaH_2PO_4$ | | | 0.1–1 g/L |
| $NaHCO_3$ | 8–30 g/L | EDTA | 0.01–10 g/L |
| $Na_2CO_3$ or $K_2CO_3$ | 0–10 g/L | $FeSO_4.7H_2O$ | 0.01–1.5 g/L. |

In accordance with specific conditions, the culture medium of the present invention may further comprise one or more ingredients selected from the group consisting of (based on 1 liter of culture solution):

| | | | |
|---|---|---|---|
| $NaNO_3$ or $KNO_3$ | 1–6 g/L | $ZnSO_4$ | 0–2 mg/L |
| $K_2SO_4$ | 0–2 g/L | $NaSeO_4$ | 0–0.03 mg/L |
| NaCl or sea salt | 0.5–1.5 g/L | $CuSO_4$ | 0–0.1 mg/L |
| $Ca(NO_3)_2$ | 0–0.1 g/L | $MoO_2$ | 0–0.05 mg/L |
| $MgSO_4$ | 0.05–0.3 g/L | $NH_4VO_3$ | 0–0.03 mg/L |
| $CaCl_2$ | 0.01–0.1 g/L | $K_2Cr_2(SO_4)_4$ | 0–0.1 mg/L |
| $H_3BO_3$ | 0–5 mg/L | $Ni(SO_4)_2$ | 0–0.1 mg/L |
| $Na_2WO_4$ | 0–0.05 mg/L | $Ti_2(SO_4)_3$ | 0–0.1 mg/L |
| $Co(NO_3)_2$ | 0–0.1 mg/L | $MnCl_2$ | 0–3 mg/L. |

(I) Preparation of Culture Solution and Inoculation (1) Providing a clean barrel, and adding an appropriate amount of clean fresh water thereto;

(2) The culture medium is added and mixing is carried out until dissolution; the supernatant is then poured into a culture vessel, and the undissolved portion is dissolved by continuously adding water and then poured into the culture vessel, the procedure is repeated until the culture medium is dissolved completely; if the culture medium is a liquid, it can be poured into the culture vessel directly and mixed with water;

(3) Adding clean water to a predetermined position;

(4) Connecting electricity, aerating to induce flow of the liquid or stirring the liquid to move, and the heating system is started when the temperature is low;

(5) The Spirulina seed prepared beforehand is shaken until the cell mass dispenses, and then poured into the culture vessel; and (6) Clean fresh water is added until the liquid level reaches the predetermined position;

(II) Cultivation

The optimum temperature for Spirulina growth is 25–37° C., and the initial inoculation is preferably carried out at nightfall, (1) Outdoor cultivation: Spirulina is a kind of photobiotic organism. It grows well when the light is sufficient; when the sunlight is too strong in Summer, however, it is necessary to shelter from light appropriately, avoiding the too high temperature caused by the too strong sunlight; if the outdoor temperature is above 37° C., sheltering from light, ventilation and cooling are necessary to maintain high growth rate; when the temperature is below 25° C., a heater is started;

(2) Indoor cultivation: if the light is insufficient, the Spirulina output may be on the low side, and the cultivation apparatus should be placed by the window that has a southern exposure, making the bottom of the vessel above the windowsill so as to make use of natural light as much as possible, if necessary, an artificial light source is started to supplement illumination; when the temperature is below 25° C., the heater is started;

(3) If there are many Spirulina cells adhering to the vessel wall, they should be brushed off the wall gently into the liquid by a brush, rendering the Spirulina cells to move again, to increase the transparency of the vessel and the illumination intensity and thus promote the growth of Spirulina;

(III) Harvest and Consumption

After about 7 days of cultivation under appropriate conditions, Spirulina can be harvested (the, dark green presenting in the vessel content indicates that Spirulina has reached the degree for harvest):

(1) Let the culture solution flow over a fine filter screen and the matured Spirulina can be filtered out;

(2) Spirulina that is filtered out and retained on the screen is rinsed with drinking water, and then can be consumed; Or before consuming an appropriate amount of warm boiled water (for example, boiled water below 70° C.) can be added and preferably keeping the Spirulina green; Or before consuming, sugar, honey, milk or fruit juice can be added to form a kind of drink, or Spirulina can be added to gruel, oatmeal or other foods for consumption;

(IV) Supplement Culture Medium or Replace Culture Solution for Further Cultivation Generally speaking, after about 25–30 days of continuous cultivation and harvest under appropriate conditions, the fresh Spirulina output begins to drop, at this moment, the culture medium should be supplemented or the culture solution should be replaced; the method for supplementing culture medium comprises: adding directly an appropriate amount of culture medium to the culture vessel, stirring until it mixes completely with the original culture solution; the method for replacing culture solution comprises:

(1) Disconnecting electricity;

(2) Discharging an appropriate amount of Spirulina liquid into a clean container for further use as Spirulina seed;

(3) Filtering out all the Spirulina cells remaining in the vessel by a fine filter screen with the filtrate discarded;

(4) The filtered out Spirulina is inoculated into the fresh culture solution for further cultivation or placed into a freezer compartment in a refrigerator for consumption in future;

(5) Discarding the liquid remaining in the vessel, and washing the inner wall of the cultivation vessel with clean water;

(6) Preparing fresh culture solution in accordance with the previous method;

(7) Connecting electricity;

(8) Taking out the Spirulina liquid that is used as Spirulina seed, filtering out the Spirulina cells by a fine filter screen with the filtrate discarded, transferring the Spirulina cells on the filter screen into the cultivation vessel, and dispensing the cells mass gently; repeating the above procedure until the Spirulina cells in the liquid are totally transferred into the cultivation vessel, at this moment, further cultivation and harvest can be carried out.

An apparatus for cultivating and consuming fresh Spirulina at home, comprising a cultivation vessel, characterized in that the cultivation vessel is equipped with an ventilation and draft tube or a stirrer, an artificial light source, an automatic temperature controller, a drain outlet and optionally a cap; the cultivation vessel and the optional cap are both transparent.

According to the habit of Spirulina, there is a need for a complete set of new methods in the following aspects to achieve the above-mentioned object: 1. Spirulina species; 2. cultivation environment and conditions; 3. cultivation and maintenance method; 4. collection and harvest of viable Spirulina; 5. consumption of fresh Spirulina; 6. storage of fresh Spirulina. The following is a detailed description of the present invention.

1. The Selection of Spirulina Species:

There are about 50 kinds of Spirulina. They differ greatly in growth characteristics and nutrients content. After comparison, "Spirulina platensis" and "Spirulina maxima" are preferred, because not only they have a complete range of nutrients but also they suit the small-scale cultivation at home. These species are commercially available from the seed domestication and cultivation base of our company. Each batch of seed can be cultivated and bred continuously for two years without variation and drop in output.

2. Cultivation Environment and Conditions at Home:

Just as the growth of other organisms, the growth of Spirulina needs adequate nutrients and favorable environment. The culture medium required by the Spirulina is inorganic compound nutrients and $CO_2$. These inorganic nutrients must meet the following three prerequisites: 1. The inorganic nutrients are capable of supplying the total nutrients required for Spirulina to reach the predetermined collection and harvest yield during the predetermined cultivation period; 2. The inorganic nutrients are capable of transforming common fresh water into water environment suit for Spirulina growth with a pH of 8–11; and 3. All the nutrients supplied for Spirulina growth must be harmless to human body. The culture medium comprises the following ingredients (based on 1 liter of culture solution):

| | | | |
|---|---|---|---|
| $K_2HPO_4$, $(Na_2)HPO_4$ or $KH_2PO_4$, $NaH_2PO_4$ | | | 0.1–1 g/L |
| $NaHCO_3$ | 8–30 g/L | EDTA | 0.01–10 g/L |
| $Na_2CO_3$ or $K_2CO_3$ | 0–10 g/L | $FeSO_4.7H_2O$ | 0.01–1.5 g/L. |

In accordance with specific conditions, the culture medium may further comprise one or more ingredients selected from the group consisting of (based on 1 liter of culture solution):

| | | | |
|---|---|---|---|
| $NaNO_3$ or $KNO_3$ | 1–6 g/L | $ZnSO_4$ | 0–2 mg/L |
| $K_2SO_4$ | 0–2 g/L | $NaSeO_4$ | 0–0.03 mg/L |
| NaCl or sea salt | 0.5–1.5 g/L | $CuSO_4$ | 0–0.1 mg/L |
| $Ca(NO_3)_2$ | 0–0.1 g/L | $MoO_2$ | 0–0.05 mg/L |
| $MgSO_4$ | 0.05–0.3 g/L | $NH_4VO_3$ | 0–0.03 mg/L |
| $CaCl_2$ | 0.01–0.1 g/L | $K_2Cr_2(SO_4)_4$ | 0–0.1 mg/L |
| $H_3BO_3$ | 0–5 mg/L | $Ni(SO_4)_2$ | 0–0.1 mg/L |
| $Na_2WO_4$ | 0–0.05 mg/L | $Ti_2(SO_4)_3$ | 0–0.1 mg/L |
| $Co(NO_3)_2$ | 0–0.1 mg/L | $MnCl_2$ | 0–3 mg/L. |

In addition, the growth of Spirulina needs appropriate illumination, temperature and $CO_2$. During the cultivation of Spirulina at home, an artificial light source (fluorescent lamp or incandescent lamp), an artificial heat source (electric heating, water heating or gas heating) and an artificial power (aeration or stirring) are employed to supplement the insufficient natural light, temperature and gas respectively. In the cultivation of Spirulina, the above-mentioned conditions and environment are realized in an appropriate apparatus. The size of the apparatus is determined in the light of the amount of Spirulina to be consumed. Generally speaking, 50–200 grams of fresh Spirulina is produced in 0.1 cubic meter of water per day. The parts of the apparatus that contact with the culture solution must be made from materials that are alkaline resisting and non-toxic. The cultivation vessel and the cap are preferably made from transparent materials such as glass or plastic.

3. Cultivation and Maintenance:

Spirulina has its own habit. Especially in the small-scale cultivation at home, the method of cultivation and maintenance affects directly the output and quality of Spirulina. The water temperature must not be lower than 20° C. when Spirulina is inoculated; after entering into the normal cultivation period, the water temperature should be controlled at 25–37° C. so that Spirulina can grow and reproduce rapidly. The vessel for cultivation of Spirulina must not be sealed, so as to allow Spirulina to respire (inhale carbon dioxide and exhale oxygen). Due to the very small size of individual Spirulina cells, they are apt to adhere to the vessel wall during growth and thus become old and die after a short period of time. Therefore, it is necessary to clean the vessel wall with a brush regularly (once a day) to render these Spirulina cells to move again.

4. Collection and Harvest of Viable Spirulina:

Seven days after the inoculation of Spirulina, it can be collected and harvested for consumption when the solution for cultivation of Spirulina has become dark green. The principle for collection and harvest is to harvest the mature Spirulina for consumption and retain the immature Spirulina for further growth so as to increase the subsequent output.

According to the selected Spirulina species, Spirulina can usually be harvested by filtration using a fine filter screen of 200–350 meshes. Generally speaking, however, the aggregates that have been old and precipitated or that floating on water are not fit for consumption (but can be used to raise fish or be used as fertilizer for flowers), and they can be filtered out using a coarse filter screen of 100–200 meshes.

5. Consumption of Fresh Spirulina:

The fresh Spirulina obtained by collection and harvest is viable, appears to be a green or dark green paste and has no foreign flavor. When being consumed, it needs to be rinsed with a small amount of drinking water with the main aim to wash away the culture solution remaining on the surface of fresh Spirulina to get a better mouth feel. The rinsed Spirulina can be consumed after adding it directly to various drinks (such as warm boiled water, milk or coffee, etc.) or adding it to other foods such as porridge, cooked wheaten foods, etc. When mixing, the temperature is preferably controlled at a temperature not higher than 50° C. to prevent some nutrients of Spirulina from being destroyed. The consumption amount of fresh Spirulina can be determined according to the specific person and the purpose of consumption. When Spirulina is used to supplement nutrients, the daily amount may be 10–30 grams per person; while when it is used for health care and therapy, the daily amount may be 30–50 grams per person. It is harmless to consume much Spirulina. The optimum time for consuming fresh Spirulina is every morning (on an empty stomach) or at bedtime.

6. Storage of Fresh Spirulina:

Since Spirulina is a kind of aquatic organism that contains high content of protein, it is apt to go bad after taken out from water (like a sea food). Therefore, the storage of Spirulina is very important. The method for storage of Spirulina comprises adding the rinsed fresh Spirulina to an appropriate amount of cool boiled water, mixing to form a dilute paste and then freezing by distributing into the ice build-up cans in freezer compartments in a refrigerator or other containers. The thus-treated fresh Spirulina can preserve freshness within a relatively long period of time. When consuming, it can be taken out of the containers according to the desired amount and added into a drink, which is convenient, fresh, interesting and healthy.

Figure 1:
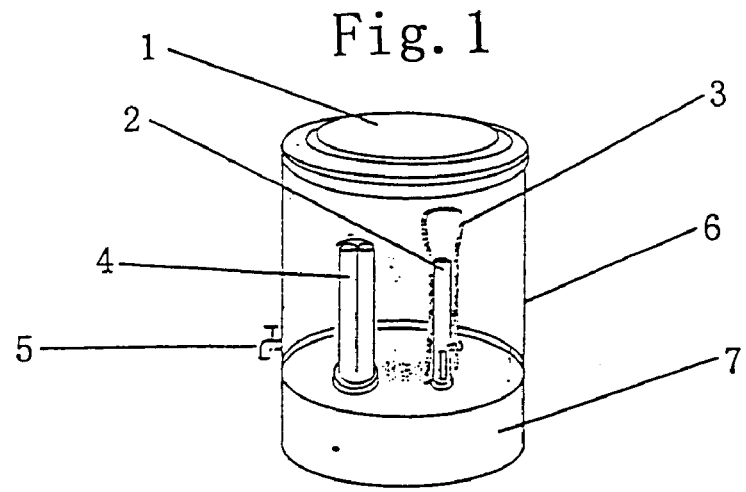
FIG. 1 shows an apparatus for implementing the present method for cultivating Spirulina.
Figure 2:
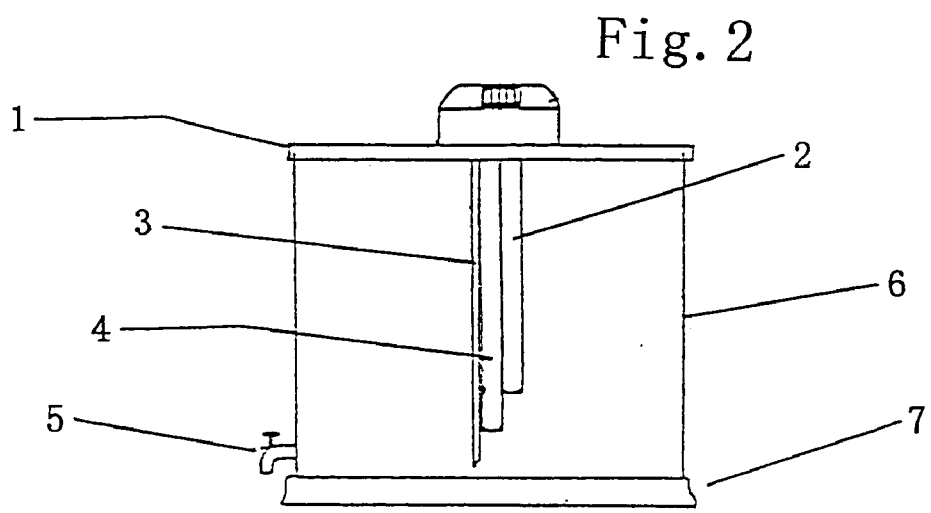
FIG. 2 shows another apparatus for implementing the present method for cultivating Spirulina.
Figure 3:
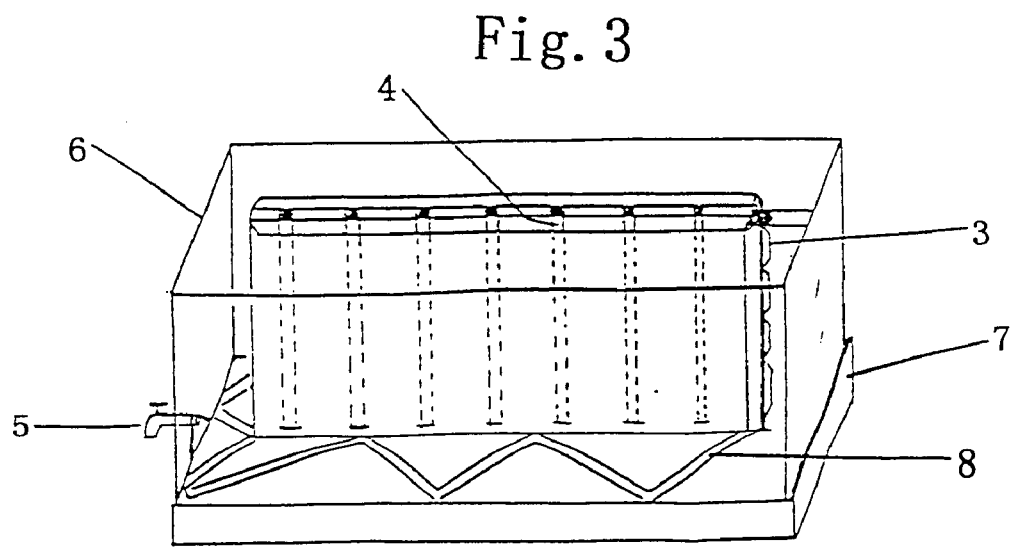
FIG. 3 shows a further apparatus for implementing the present method for cultivating Spirulina.

Reference sign 1 stands for a cap that serves the function of dust prevention and allows gas to pass through;

Reference sign 2 stands for a automatic temperature controller that is used to control the temperature of the culture solution; when the temperature is below 25° C., it begins to heat the liquid automatically;

Reference sign 3 stands for a ventilation and draft tube that is used to stir and circulate the liquid to render Spirulina to move, it runs continuously;

Reference sign 4 stands for an artificial light source that is used to supplement the illumination at night or when there is no illumination;

Reference sign 5 stands for a drain outlet that is used to collect fresh Spirulina, discharge or replace the culture solution in the cultivation vessel;

Reference sign 6 stands for a transparent cultivation vessel;

Reference sign 7 stands for a foundation support; and

Reference sign 8 stands for a heating body.

DESCRIPTION OF THE PREFERRED EMBODIMENTS

The present invention is described in further detail in the following non-limiting examples with reference to the accompanying drawings.

EXAMPLE 1 (SEE FIG. 1)

I. Preparation of Culture Solution and Inoculation

1. A clean barrel was provided, and 10 liters of clean water was added thereto;
2. The culture medium was added and mixing was carried out until dissolution; the supernatant was then poured into a culture vessel (6), and the undissolved portion was dissolved by continuously adding water and then poured into the culture vessel (6), the procedure was repeated until the culture medium was dissolved completely; if the culture medium was a liquid, it could be poured into the culture vessel (6) directly and mixed with water;
3. Clean water was added to a position corresponding to ⅔ of the volume of the culture vessel (6);
4. Electricity was connected, and the ventilation and draft tube (3) begun to bubble up, and the automatic temperature controller (2) begun to heat the liquid automatically when the temperature was low;
5. The Spirulina seed prepared beforehand was shaken gently until the cell mass dispensed, and then poured into the culture vessel (6);
6. Clean water was added until the liquid level reached a position that was 3–5 centimeters from the top of the culture vessel (6).

II. Cultivation

The optimum temperature for Spirulina growth was 25–37° C., and the initial inoculation was preferably carried out at nightfall, 1. Outdoor cultivation: Spirulina is a kind of photobiotic organism. It grew well when the light was sufficient; when the sunlight was too strong in Summer, however, it was necessary to shelter from light appropriately, avoiding the too high temperature caused by the too strong sunlight; if the outdoor temperature was above 37° C., sheltering from light, ventilation and cooling were necessary to maintain high growth rate; when the temperature was below 25° C., the automatic temperature controller (2) begun to heat the liquid automatically;
2. Indoor cultivation: if the light was insufficient, the Spirulina yield might be on the low side, and the cultivation apparatus should be placed by the window that had a southern exposure, making the bottom of the vessel above the windowsill so as to make use of natural light as much as possible, if necessary, an artificial light source (4) was started to supplement illumination; when the temperature was below 25° C., the automatic temperature controller (2) begun to heat the liquid automatically;
3. If there were many Spirulina cells adhering to the vessel wall, they should be brushed off the wall gently into the liquid by a brush, rendering the Spirulina cells to move again, and thus promote the growth of Spirulina.

III. Harvest and Consumption

After about 7 days of cultivation under appropriate conditions, Spirulina could be harvested (the dark green presenting in the vessel content indicated that Spirulina had reached the degree for harvest):

1. The drain outlet (5) was opened, let the culture solution flow over a filter screen of 300 meshes and the matured Spirulina was filtered out;
2. Spirulina that was filtered out and retained on the screen was rinsed with drinking water, and then was consumed; Or before consuming, an appropriate amount of warm boiled water below 50° C. and preferable cold water was added and keeping the Spirulina green; Or before consuming, sugar, honey, milk or fruit juice etc. was added to form a kind of drink, or Spirulina was added to gruel, oatmeal or other foods for consumption.

IV. Supplement Culture Medium or Replace Culture Solution for Further Cultivation Generally speaking, after about 25–30 days of continuous cultivation and harvest under appropriate conditions, the fresh Spirulina yield begun to drop, at this moment, the culture medium should be supplemented or the culture solution should be replaced; the method for supplementing culture medium comprised: an appropriate amount of culture medium was added directly to the culture vessel (6), stirring was carried out until it mixed completely with the original culture solution; the method for replacing culture solution comprised:

1. Electricity was disconnected;
2. About ½ to ⅔ vessel of Spirulina liquid was discharged into a clean container for further use as Spirulina seed;
3. All of the Spirulina cells remaining in the vessel were filtered out by a fine filter screen of 300 meshes and the filtrate was discarded;
4. The filtered out Spirulina was inoculated into the fresh culture solution for further cultivation or placed into a freezer compartment in a refrigerator for consumption in future;
5. The liquid remaining in the vessel was discarded, and the inner wall of the cultivation vessel (6) was washed gently with wet flannelette and clean water;
6. Fresh culture solution was prepared in accordance with the previous method;
7. Electricity was connected;
8. The Spirulina liquid that was used as Spirulina seed was taken out, the Spirulina cells was filtered out by a fine filter screen of 300 meshes with the filtrate discarded, the Spirulina cells on the filter screen were transferred into the cultivation vessel (6), and the cells mass was dispensed gently; the above procedure was repeated until the Spirulina cells in the liquid were totally transferred into the cultivation vessel (6), at this moment, further cultivation and harvest could be carried out.

EXAMPLE 2 (SEE FIG. 2)

Cultivation Method

I. Inoculation

1. A clean barrel was provided, and an appropriate amount of clean water was added thereto;

2. The prepared culture medium was added and mixing was carried out until dissolution; the supernatant was then poured into a culture vessel (6), and the undissolved portion was dissolved by continuously adding water and then poured into the culture vessel (6), the procedure was repeated until the culture medium was dissolved completely; if the culture medium was a liquid, it was poured into the culture vessel (6) directly and mixed with water;
3. Clean water was added to a position corresponding to ⅔ of the volume of the culture vessel (6);
4. Electricity was connected, and the ventilation and draft tube (3) begun to bubble up, and the automatic temperature controller (2) begun to heat the liquid automatically when the temperature was low;
5. The Spirulina seed prepared beforehand was shaken gently until the cell mass dispensed, and then poured into the culture vessel (6);
6. Clean water was added until the liquid level reached a position that was 3–5 centimeters from the top of the culture vessel (6).

II. Cultivation

1. Outdoor cultivation: Spirulina is a kind of photobiotic organism. It grew well when the light was sufficient; when the sunlight was too strong in Summer, however, it was necessary to shelter from light appropriately, avoiding the too high temperature caused by the too strong sunlight; if the outdoor temperature was above 37° C., sheltering from light, ventilation and cooling were necessary to maintain high growth rate; when the temperature was below 25° C., the automatic temperature controller (2) begun to heat the liquid automatically;
2. Indoor cultivation: if the light was insufficient, the Spirulina yield might be on the low side, and the cultivation apparatus should be placed by the window that had a southern exposure, making the bottom of the vessel above the windowsill so as to make use of natural light as much as possible, if necessary, an artificial light source (4) was started to supplement illumination; when the temperature was below 25° C., the automatic temperature controller (2) begun to heat the liquid automatically;
3. If there were many Spirulina cells adhering to the vessel wall, they should be brushed off the wall gently into the liquid by a brush, rendering the Spirulina cells to move again, and thus promote the growth of Spirulina.

III. Harvest and Consumption

1. The drain outlet (5) was opened, let the culture solution flow over a filter screen of 300 meshes and the matured Spirulina was filtered out;
2. Spirulina that was filtered out and retained on the screen was rinsed with drinking water, and then was consumed; Or before consuming, an appropriate amount of boiled water below 50° C. was added and keeping the Spirulina green or slight brown; Or before consuming, sugar, honey, milk or fruit juice etc. was added to form a kind of drink, or Spirulina was added to gruel, oatmeal or other foods for consumption.

IV. Supplement Culture Medium or Replace Culture Solution for Further Cultivation Generally speaking, after about 25–30 days of continuous cultivation and harvest under appropriate conditions, the fresh Spirulina yield begun to drop, at this moment, the culture medium should be supplemented or the culture solution should be replaced; the method for supplementing culture medium comprised: an appropriate amount of culture medium was added directly to the culture vessel (6), stirring was carried out until it mixed completely with the original culture solution; the method for replacing culture solution comprised:

1. Electricity was disconnected;
2. About ½ to ⅔ vessel of Spirulina liquid was discharged into a clean container for further use as Spirulina seed;
3. All of the Spirulina cells remaining in the vessel were filtered out by a fine filter screen of 300 meshes with the filtrate discarded;
4. The filtered out Spirulina was inoculated into the fresh culture solution for further cultivation or placed into a freezer compartment in a refrigerator for consumption in future;
5. The liquid remaining in the vessel was discarded, and the inner wall of the cultivation vessel (6) was washed gently with wet flannelette and clean water;
6. Fresh culture solution was prepared in accordance with the previous method;
7. Electricity was connected;
8. The Spirulina liquid that was used as Spirulina seed was taken out, the Spirulina cells was filtered out by a fine filter screen of 300 meshes with the filtrate discarded, the Spirulina cells on the filter screen was transferred into the cultivation vessel (6), and the cells mass was dispensed gently; the above procedure was repeated until the Spirulina cells in the liquid were totally transferred into the cultivation vessel (6), at this moment, further cultivation and harvest could be carried out.

EXAMPLE 3 (SEE FIG. 3)

Cultivation Method

I. Inoculation

1. A clean barrel was provided, and an appropriate amount of clean water was added thereto;
2. The prepared culture medium was added and mixing was carried out until dissolution; the supernatant was then poured into a culture vessel (6), and the undissolved portion was dissolved by continuously adding water and then poured into the culture vessel (6), the procedure was repeated until the culture medium was dissolved completely; if the culture medium was a liquid, it was poured into the culture vessel (6) directly and mixed with water;
3. Clean water was added to a position corresponding to ⅔ of the volume of the culture vessel (6);
4. Electricity was connected (in the case of horizontal vessel, it was necessary to connect a stirrer to the electricity), and the automatic temperature controller (2) begun to heat the liquid automatically when the temperature was low;
5. The Spirulina seed prepared beforehand was shaken gently until the cell mass dispensed, and then poured into the culture vessel (6);
6. Clean water was added until the liquid level reached a position that was 3–5 centimeters from the top of the culture vessel (6).

II. Cultivation

1. Outdoor cultivation: Spirulina is a kind of photobiotic organism. It grew well when the light is sufficient; when the sunlight was too strong in Summer, however, it was necessary to shelter from light appropriately, avoiding the too high temperature caused by the too strong sunlight; if the outdoor temperature was above 37° C., sheltering from light, ventilation and cooling were necessary to maintain high growth rate; when the temperature was below 25° C., the heating body (8) begun to heat the liquid automatically;
2. Indoor cultivation: if the light was insufficient, the Spirulina yield might be on the low side, and the cultivation apparatus should be placed by the window that had a southern exposure, making the bottom of the vessel above the windowsill so as to make use of natural light as much as possible, if necessary, an artificial light source (4) was started to supplement illumination; when the temperature was below 25° C., the automatic temperature controller (2) begun to heat the liquid automatically;
3. If there were many Spirulina cells adhering to the vessel wall, they should be brushed off the wall gently into the liquid by a brush, rendering the Spirulina cells to move again and thus grow.

III. Harvest and Consumption

1. The drain outlet (5) was opened, let the culture solution flow over a filter screen of 300 meshes and the matured Spirulina was filtered out;
2. Spirulina that was filtered out and retained on the screen was rinsed with drinking water, and then was consumed; Or before consuming, an appropriate amount of boiled water below 50° C. was added and keeping the Spirulina green or slight brown; Or before consuming, sugar, honey, milk or fruit juice etc. was added to form a kind of drink, or Spirulina was added to gruel, oatmeal or other foods for consumption.

IV. Supplement Culture Medium or Replace Culture Solution for Further Cultivation Generally speaking, after about 25–30 days of continuous cultivation and harvest under appropriate conditions, the fresh Spirulina yield begun to drop, at this moment, the culture medium should be supplemented or the culture solution should be replaced; the method for supplementing culture medium comprised: an appropriate amount of culture medium was added directly to the culture vessel (6), stirring was carried out until it mixed completely with the original culture solution; the method for replacing culture solution comprised:

1. Electricity was disconnected;
2. About 1/3 to 2/3 vessel of Spirulina liquid was discharged into a clean container for further use as Spirulina seed;
3. All of the Spirulina cells remaining in the vessel were filtered out by a fine filter screen of 300 meshes with the filtrate discarded;
4. The filtered out Spirulina was inoculated into the fresh culture solution for further cultivation or placed into a freezer compartment in a refrigerator for consumption in future;
5. The liquid remaining in the vessel was discarded, and the inner wall of the cultivation vessel (6) was washed gently with wet flannelette and clean water;
6. Fresh culture solution was prepared in accordance with the previous method;
7. Electricity is connected;
8. The Spirulina liquid that was used as Spirulina seed was taken out, the Spirulina cells were filtered out by a fine filter screen of 300 meshes with the filtrate discarded, the Spirulina cells on the filter screen was transferred into the cultivation vessel (6), and the cells mass was dispensed gently; the above procedure was repeated until the Spirulina cells in the liquid were totally transferred into the cultivation vessel (6), at this moment, further cultivation and harvest could be carried out.

It should be appreciated by a person skilled in the art that the foregoing examples are not intended to define the scope of the present invention but to describe the present invention in further detail. The spirit or scope of the present invention is defined in the appended claims. Various modifications and changes not departing from the spirit of the invention are within the scope of the present invention.

INDUSTRIAL PRACTICABILITY

The effects of the present invention are as follows:

1. The cultivation of Spirulina at home can achieve the consumption of fresh viable Spirulina, prevent effectively the rare nutrients of Spirulina from being destroyed during the industrial processing (dehydration, drying) and increase the nutritive value. Moreover, the fresh Spirulina has no stinking smell as of rotten fish in the dried products of Spirulina.
2. Human body can absorb fresh Spirulina much easily than dried products. The absorptivity for fresh Spirulina is more than 98% while the absorptivity for dried products is only about 78%.
3. The present invention effectively reduces the damage to human body caused by counterfeit and inferior Spirulina products. The commercially available dried products of Spirulina are all processed end products, some of which need to add non-Spirulina substances such as additives etc. and thus are apt to be faked; while Spirulina cultivated at home can be consumed directly, putting an end to the damage caused by counterfeit and inferior products.
4. For the same amount of nutrients that can be digested and absorbed by human body, the cost of fresh Spirulina is only 20–50% of that of commercially available dried products of Spirulina.
5. Spirulina is a kind of rapid-reproducing photosynthetic organism that releases large amount of natural oxygen and absorbs large amount of $CO_2$ during cultivation, which contributes to the improvement on air quality in room.

What is claimed is:

1. A domestic culturing method for producing and consuming fresh Spirulina and improving air quality in a room, comprising the following steps:
   (a) seeding viable pure Spirulina cells into a water soluble culture medium containing inorganic compound nutrients and having a pH of 8–11;
   (b) injecting the resulting culture solution containing the Spirulina cells into a domestic electrical appliance equipped with an artificial light source, an automatic temperature controller and a ventilation and draft tube or a stirrer, allowing the Spirulina cells to grow and proliferate for a period of time at a culture solution temperature of 25–40° C.

(c) collecting matured Spirulina cells from the culture solution by filtration using a fine filter screen and allowing unmatured Spirulina cells to pass through to grow further; optionally, collecting and storing released oxygen by a cap fitted onto the electrical appliance and being in the form of a flexible pocket, or a rigid chamber for supplying to a person in need thereof, or otherwise releasing from the electrical appliance, oxygen regularly and quantitatively; if necessary, removing old Spirulina cells and precipitate using a coarse filter screen; and (d) consuming directly the filtered-out viable matured Spirulina cells after they are rinsed with water; or storing immediately the filtered-out viable Spirulina cells for further use by freezing after they are rinsed with water; or formulating the collected viable Spirulina cells into a paste with cold water and then storing by freezing.

2. The method as set forth in claim 1, wherein the Spirulina is Spirulina platensis or Spirulina maxima.

3. The method as set forth in claim 1 or claim 2, wherein the culture solution temperature in step (b) is 25–37° C.

4. The method as set forth in claim 1 or claim 2, wherein in step (b) the Spirulina cells are allowed to grow for about 7 days in a first cycle.

5. The method as set forth in claim 1 or claim 2, wherein in step (c) the culture medium is supplemented or replaced after 25–30 days of continuous collection.

6. The method as set forth in claim 1 or claim 2, wherein in step (c) the fine filter screen is one of 200–350 meshes and the coarse filter screen is one of 100–200 meshes.

7. The method as set forth in claim 1 or claim 2, wherein in step (d), after rinsing with water, the filtered-out viable Spirulina cells are mixed with a drink or added to food and then consumed.

8. The method as set forth in claim 7, wherein the drink comprises milk, coffee or juice, and the food comprises gruel, oatmeal, sugar or honey.

9. The method as set forth in claim 1 or 2, wherein based on 1 liter of culture solution, the culture medium contains the following ingredients:

| | |
|---|---|
| $K_2HPO_4(Na_2)HPO_4$ or $KH_2PO_4$, $NaH_2PO_4$ | 0.1–1 g/L |
| $NaHCO_3$ | 8–30 g/L |
| $Na_2CO_3$ or $K_2CO_3$ | 0–10 g/L. |

10. The method as set forth in claim 9, wherein based on 1 liter of culture solution, the culture medium further contains one or more ingredients selected from the group consisting of:

| | | | |
|---|---|---|---|
| EDTA | 0.01–10 g/L, | $FeSO_4.7H_2O$ | 0.01–1.5 g/L, |
| $NaNO_3$ or $KNO_3$ | 1–6 g/L, | $ZnSO_4$ | 0–2 mg/L, |
| $K_2SO_4$ | 0–2 g/L, | $NaSeO_4$ | 0–0.03 mg/L, |
| NaCl or sea salt | 0.5–1.5 g/L, | $CuSO_4$ | 0–0.1 mg/L, |
| $Ca(NO_3)_2$ | 0–0.1 g/L, | $MoO_2$ | 0–0.05 mg/L, |
| $MgSO_4$ | 0.05–0.3 g/L, | $NH_4VO_3$ | 0–0.03 mg/L, |
| $CaCl_2$ | 0.01–0.1 g/L, | $K_2Cr_2(SO_4)_4$ | 0–0.1 mg/L, |
| $H_3BO_3$ | 0–5 mg/L, | $Ni(SO_4)_2$ | 0–0.1 mg/L, |
| $Na_2WO_4$ | 0–0.05 mg/L, | $Ti_2(SO_4)_3$ | 0–0.1 mg/L, |
| $CO(NO_3)_2$ | 0–0.1 mg/L, and | $MnCl_2$ | 0–3 mg/L. |

\* \* \* \* \*